US008262288B2

(12) United States Patent
Shaughnessy

(10) Patent No.: US 8,262,288 B2
(45) Date of Patent: Sep. 11, 2012

(54) FOCAL SPOT POSITION DETERMINER

(75) Inventor: Charles Shaughnessy, Hamilton, MA (US)

(73) Assignee: Analogic Corporation, Peabody, MA (US)

( * ) Notice: Subject to any disclaimer, the term of this patent is extended or adjusted under 35 U.S.C. 154(b) by 295 days.

(21) Appl. No.: 12/691,358

(22) Filed: Jan. 21, 2010

(65) Prior Publication Data

US 2011/0176663 A1 Jul. 21, 2011

(51) Int. Cl.
*G01D 18/00* (2006.01)
(52) U.S. Cl. .......................................... 378/207; 378/154
(58) Field of Classification Search ................... 378/147, 378/149, 150, 154, 207
See application file for complete search history.

(56) References Cited

U.S. PATENT DOCUMENTS

| | | | |
|---|---|---|---|
| 4,472,827 A | 9/1984 | Gabbay et al. | |
| 5,668,851 A | 9/1997 | Dobbs | |
| 5,745,548 A * | 4/1998 | Dobbs et al. | 378/207 |
| 5,753,917 A | 5/1998 | Engdahl | |
| 5,781,606 A | 7/1998 | Dobbs et al. | |
| 6,175,615 B1 | 1/2001 | Guru et al. | |
| 6,362,479 B1 | 3/2002 | Andreaco et al. | |
| 6,448,559 B1 | 9/2002 | Saoudi et al. | |
| 6,980,629 B1 | 12/2005 | Hoheisel et al. | |
| 7,141,812 B2 | 11/2006 | Appleby et al. | |
| 7,609,804 B2 | 10/2009 | Hoffman | |
| 2004/0120464 A1 | 6/2004 | Hoffman | |
| 2009/0039562 A1 | 2/2009 | Freund et al. | |

FOREIGN PATENT DOCUMENTS

GB 536449 5/1941

OTHER PUBLICATIONS

G. Vogtmeier et al, "Two-Dimensional Anti-scatter grids for computed tomography detectors", Proc. SPIE vol. 6913, 691359-1, 2008.
International Search Report cited in related application No. PCT/US2009/051201 dated Mar. 24, 2010.
Notification Concerning Transmittal of International Preliminary Report on Patentability (Chapter 1 of the Patent Cooperation Treaty) cited in related application No. PCT/US2009/051201 dated Feb. 2, 2012.

* cited by examiner

*Primary Examiner* — Jurie Yun
(74) *Attorney, Agent, or Firm* — Cooper Legal Group LLC

(57) ABSTRACT

One or more systems and/or techniques are disclosed herein for determining the orientation of a focal spot of a radiation source based upon shadows that are imposed on channels of a detector array from an anti-scatter grid. The anti-scatter grid is comprised of one or more anti-scatter plates that are focused on a point other than an intended focal spot of the radiation source. Such anti-scatters plates cast shadows on the detector array (even when the focal spot is located at the intended focal spot). By measuring changes in the signals generated by channels of the detector array that detect the shadows, it may be determined how the orientation of the focal spot has changed throughout an examination or between a calibration scan and an examination scan, for example.

20 Claims, 5 Drawing Sheets

FOCAL SPOT POSITION DETERMINER

BACKGROUND

The present application relates to radiation scanners, such as computed tomography (CT) scanners. It finds particular application with radiation scanners that comprise anti-scatters grids (also referred to as anti-scatter collimators) including one- and two-dimensional type grids.

CT and other radiography imaging systems are useful to provide information, or images, of targets (e.g., interior aspects) of an object under examination. Generally, the object is exposed to radiation, and an image is formed based upon the radiation absorbed by the targets, or rather an amount of radiation that is able to pass through the targets. Typically, highly dense targets absorb more radiation than less dense targets, and thus a target having a higher density, such as a bone or mass, for example, will be apparent when surrounded by less dense targets, such as fat tissue or muscle.

A radiation scanner typically comprises a detector array and a radiation source respectively mounted on diametrically opposing sides of an examination region within which the object under examination resides. In some scanners, such as three-dimensional imaging scanners (e.g., CT scanners), for example, the detector array and radiation source are mounted on opposing sides of a rotating gantry that forms a ring, or donut, around the object under examination. The rotating gantry (including the radiation source and/or detector array) is configured to be rotated in a circle situated within an x,y plane about an axis extending in the z-dimension (e.g., an "isocenter" and/or direction within which a focal spot of the scanner may "drift") during an examination of the object (e.g., an object under examination, such as a suitcase, moves in the z-direction as it is moved into the scanner by a conveyor belt). As the rotating gantry is rotated, radiation can be intermittently or continuously emitted from a focal spot of the radiation source.

Radiation that traverses an object under examination is detected by one or more channels (also commonly referred to as pixels) of the detector array and respective signals are generated in response thereto. The signals are indicative of characteristics of the radiation that is detected by the respective channels, and thus is indicative of the attenuation of the object from a particular view, or projection.

In an ideal environment, the radiation that is detected by a channel of the detector array corresponds to attenuated radiation that strikes the channel on a straight axis from the focal spot of the radiation source. This type of radiation is commonly referred to as primary radiation. However, due to inevitable interactions with the object and/or radiation scanner, typically some of the radiation that is detected has deviated from the straight axis. Radiation that has deviated from the straight axis is commonly referred to as scattered radiation or secondary radiation. It will be appreciated that the detection of secondary radiation is undesirable because it can increase noise in a signal generated from the channel detecting the secondary radiation and/or it can reduce the quality of an image yielded from the signal.

In order to reduce the amount of secondary radiation that is detected by channels of the detector array, anti-scatter grids are commonly inserted between the examination region and the detector array. The anti-scatter grids are comprised of a plurality of anti-scatter plates configured to absorb secondary radiation and a plurality of transmission channels configured to allow primary radiation to pass through the grid and be detected by a channel of the detector array.

While the anti-scatter grids have proven effective for capturing secondary radiation, anti-scatter plates can impose shadows on the detector array. Such shadows can be detected by channels of the detector array and can create errors in the signals that are respectively generated by shadowed channels. If affected signals, or information derived from such signals, are not corrected (e.g., to take into account the shadowing), the shadowing may result in artifacts in an image yielded from the signals.

An air table(s) (also referred to as a calibration table) is commonly used to compensate for, or reduce the effects of, errors in the signals, including errors generated because of shadowing. During a calibration scan (e.g., a scan in which no object is present), signals generated by the respective channels are measured, and the measurements are stored in the air table(s). During examination scans (e.g., scans in which an object is present), the signals generated by respective channels are measured and compared with the measurement(s) stored in the air table(s) for the respective channels. The attenuation of radiation that is represented by the signal is determined by measuring the difference between the measurement(s) stored in the air table(s) and the measurement(s) generated during an examination scan. In this way, the portion of the signal indicative of the attenuation of radiation can be identified, for example.

The measurements acquired during the calibration scan and stored in the air table(s) are useful for compensating for errors in a signal as long as the errors are substantially static during the calibration scan and the examination scan(s). However, if the errors produced during a calibration scan and the errors produced during one or more examination scans differ, the difference between the measurement(s) stored in the air table(s) and the measurement(s) generated during the one or more examination scans may not be indicative of the attenuation of radiation. Stated differently, the measurements acquired during the calibration scan may not be accurate measurements for calibrating the respective channels (e.g., because a baseline value of the error in a signal has changed between the calibration scan and the one or more examination scans).

One common reason the signal can change between the calibration scan and one or more examination scans (or even change during a single examination scan) is due to dynamic shadowing. Dynamic shadowing occurs when the orientation of a shadow imposed on a channel by an anti-scatter plate changes between the calibration scan and the examination scan or between a first view of an examination scan and a second view of the same examination scan. It is commonly caused by focal spot motion (e.g., a change in the orientation of the focal spot with respect to the detector array). Such focal spot motion can be caused by thermal drift that occurs as the radiation source heats up and/or cools down during a scan, for example.

If the shadow imposed on a channel by an anti-scatter plate changes between the calibration scan and the examination scan, the measurement(s) stored in the air table(s) for the channel is typically adjusted before a correction mechanism uses the measurement(s) to isolate useful information in the signal from the errors. The adjusted measurement(s) reflects a (predicted) measurement(s) that would have been acquired during the calibration scan had the focal spot been oriented substantially similarly to its orientation during the examination scan.

To identify dynamic shadowing and determine how to accurately adjust the measurement(s) stored in the air table (s), the orientation of the focal spot is typically monitored, or rather calculated. Conventionally, a pin-hole camera placed near the radiation source has been configured to monitor the orientation (e.g., shape, position, etc.) of the fan, cone, or other shaped beam that impinges the detector array during the examination. The orientation of the focal spot can be determined based upon the orientation of the beam that is cast from the focal spot. A correction mechanism can then predict the orientation of shadows cast by the anti-scatter plates on respective channels and recalculate, or adjust, the air table measurement(s) for respective channels so that the attenuation caused by radiation can be determined from signals generated during an examination scan. In this way, the air table(s) comprises estimated measurements for respective channels that would have been produced during the calibration scan if the orientation of the focal spot during the calibration scan was substantially similar to the orientation of the focal spot during the examination scan.

While the use of a pin-hole camera to detect the orientation of the focal spot has proven successful in some applications, there are some drawbacks to such a technique. For example, it is typically difficult to make corrections to the signals, or information derived therefrom, on a view-by-view basis in real-time because of the complex calculations required to determine the orientation of the focal spot from a pin-hole camera image and to predict the orientation of the shadows produced based upon a determined focal spot orientation. Therefore, the pin-hole camera technique is typically limited to applications that use low resolution, slow-moving or stationary scanners. Additionally, making a determination about the orientation of the focal spot from a pin-hole camera image is not precise. Thus, corrections made to the signals, or resulting information, may be inaccurate. Such inaccuracies may result in artifacts being introduced.

SUMMARY

Aspects of the present application address the above matters, and others. According to one aspect, a radiography scanning apparatus is provided. The apparatus comprises a radiation source configured to emit radiation and a detector array configured to detect the emitted radiation. The apparatus further comprises an anti-scatter grid comprised of a plurality of anti-scatter plates, wherein a first set of anti-scatter plates are focused on a point other than an intended focal spot of the radiation source, and wherein a second set of anti-scatter plates are focused on the intended focal spot, the second set different than the first set.

According to another aspect, a method is provided. The method comprises receiving a signal that was generated by a calibration channel of a detector array during a calibration scan and receiving a signal that was generated by the calibration channel of the detector array during an examination scan. The method also comprises determining an orientation of a focal spot during the examination scan based on the signal that was generated by the calibration channel during the calibration scan and the signal that was generated by the calibration channel during the examination scan. The method further comprises receiving a signal that was generated by an imaging channel of the detector array during the examination and correcting at least one of the signals that was generated by the imaging channel during the examination and projection data yielded from the signal that was generated by the imaging channel during the examination, the correction based upon the determined orientation of the focal spot during the examination.

According to yet another aspect, a radiography apparatus is provided. The apparatus comprises a radiation source configured to emit radiation and an anti-scatter grid comprised of at least first and second sets of anti-scatter plates. The first set comprises anti-scatter plates that are focused on a point other than an intended focal spot of the radiation source and then second set comprises anti-scatter plates that are focused on the intended focal spot of the radiation source. The apparatus further comprises a detector array configured to detect the emitted radiation, the detector array comprising calibration channels and imaging channels. Respective calibration channels are positioned in close spatial proximity to an anti-scatter plate that is focused on a point other than the intended focal spot of the radiation source, and respective imaging channels are positioned in close spatial proximity to an anti-scatter plate that is focused on the intended focal spot of the radiation source. The calibration channels are respectively configured to generate signals indicative of an orientation of a focal spot. The apparatus also comprises a correction component configured to identify a change in the orientation of the focal spot between a calibration scan and an examination scan based upon the signals generated by the calibration channels.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
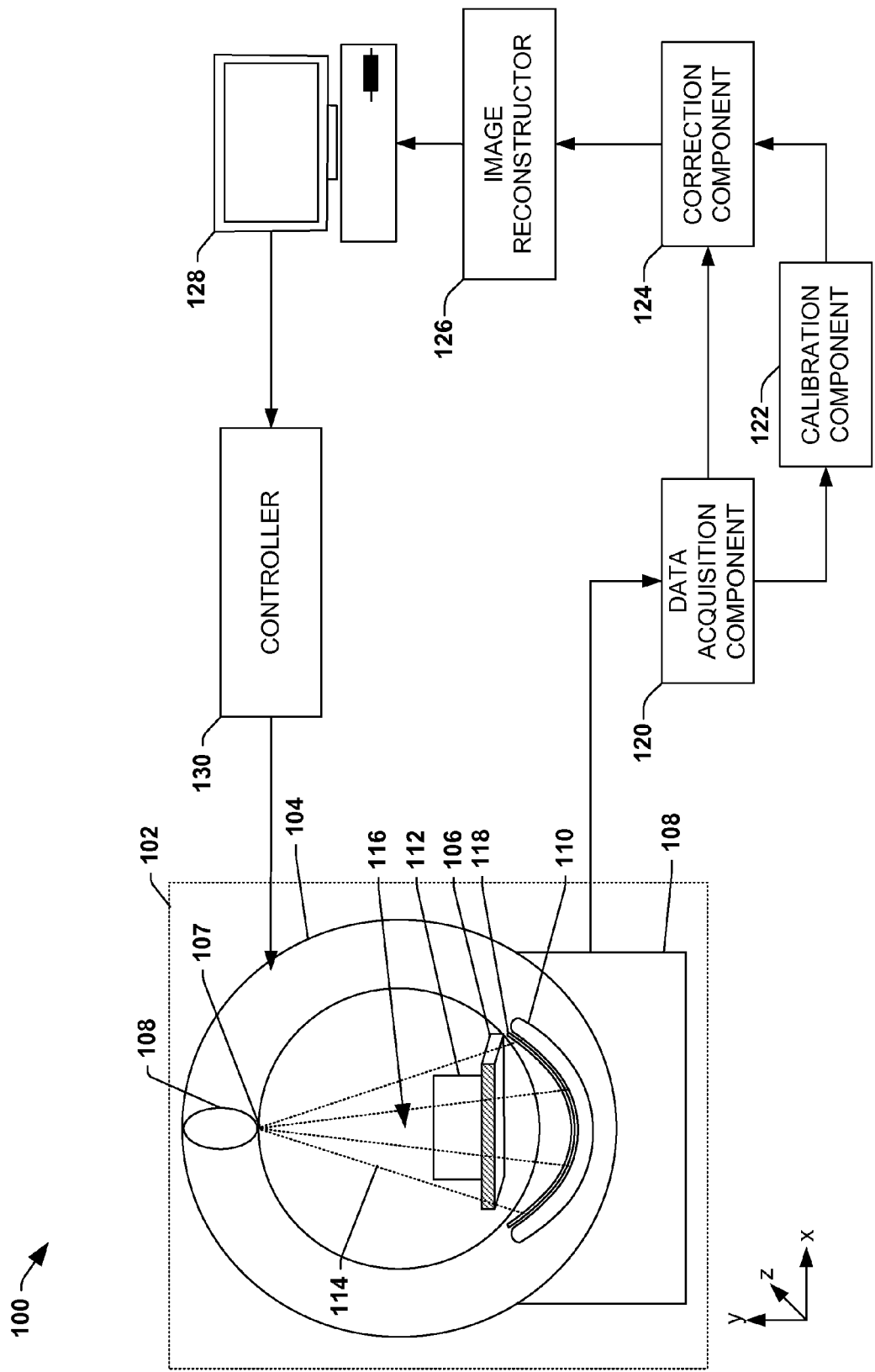
FIG. 1 depicts a schematic block diagram of an example scanner.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for identifying changes in the orientation of a focal spot and/or changes in the shadowing of channels of a detector array by an anti-scatter grid are provided herein. In this way, signals generated by the channels, or information derived therefrom, that are indicative of shadowing may be corrected to reduce artifacts in an image yielded from the signals, for example.

FIG. 1 depicts an example scanner 100 that may be useful in medical, security, or industrial applications, for example. As illustrated, the scanner 100 typically comprises an object scanning apparatus 102. In one embodiment, the object scanning apparatus 102 is a third generation computed tomography (CT) scanner that comprises a rotating gantry 104 and an examination surface 106, such as a bed or conveyor (e.g., going into and out of the page). It will be appreciated that while reference is made to a third generation CT scanner, other radiation scanners such as fourth generation CT scanners, line scanners, etc. are also contemplated.

The rotating gantry 104 comprises a radiation source 108 (e.g., an x-ray tube) and a detector array 110 and can be configured to rotate relative to the examination surface 106 about an axis of rotation (e.g., an isocenter) perpendicular to the plane of the page (e.g., into/out of the page). During an examination, a focal spot 107 of the radiation source 108 emits a fan, cone, wedge, or other shaped beam of radiation 114 that traverses an object 112 situated on the examination surface 106 in an examination region 116 of the object scanning apparatus 102. In this way, projections of a leg or a suitcase, for example, can be collected from a scan of the object 112.

Radiation 114 that traverses the object 112 is detected by the detector array 110. It will be appreciated that numerous compositions for the detector array 110 are known to those skilled in the art and may be suitable for the example scanner 100. For example, the detector array 110 may comprise a direct conversion detector material, such as a crystalline material (e.g., cadmium zinc telluride, cadmium telluride) and/or an amorphous photoelectric material. Alternatively, the detector array 110 may be a solid state detector comprised of scintillating crystals and a two-dimensional array of photodiodes configured to receive light photons generated by the scintillator in response to radiation 114 from the focal spot 107 of the radiation source 108.

Generally, the detector array 110 is comprised of a plurality of (interchangeable) detector modules that are positioned to form an arcuate structure. Respective detector modules comprise a plurality of channels (also referred to as pixels) that are respectively configured to detect radiation that impinges the detector array in close spatial proximity to the location of the channel on the detector array 110. It will be appreciated that while reference is made to an arcuate detector array comprised of a plurality of detector modules, other configurations are also contemplated. For example, in another embodiment, the detector array 110 can be comprised of a single, rectangular detector module that substantially spans the length of the detector array 110 and comprises a plurality of channels.

The channels are configured to detect radiation 114 and generate signals, or pulses (hereinafter collectively referred to as signals), in response thereto that are indicative of the detected radiation. To reduce the amount of secondary radiation that is detected by the respective channels (and reduce noise in signals generated by the channels), an anti-scatter grid 118 (also referred to as an anti-scatter collimator) is situated in the example scanner 100 between the examination region 116 and the detector array 110. The anti-scatter grid 118 is configured to absorb, or otherwise alter secondary radiation, so that it is not detected by channels of the detector array 110, while allowing primary radiation to pass through.

As will be discussed in more detail with regards to FIGS. 2-3, the anti-scatter grid 118 is generally comprised of one or more anti-scatter modules (not shown), and the anti-scatter grid 118 can be assembled by joining adjacent anti-scatter modules together, for example. It will be appreciated that the number of modules may depend on the application and/or on assembly preferences (e.g., whether it is more economical to make a single, larger module, or many smaller modules), for example. In one embodiment, the number of anti-scatter modules is a function of the number of detector modules that comprise the detector array 110. In this way, respective anti-scatter modules may be attached to a detector module prior to assembly of the detector array 110, for example.

Signals that are produced by channels of the detector array 110 can be transmitted from the detector array 110 to a data acquisition component 120 configured to compile signals that were transmitted within a predetermine time interval, or measurement interval, using techniques known to those skilled in the art (e.g., binning). It will be appreciated that such a measurement interval may be referred to as a "view" and generally reflects signals generated from radiation 114 that was emitted while the radiation source 108 was at a particular angular range relative to the object 112. Based upon the compiled signals, the data acquisition component 120 can generate projection data indicative of the compiled signals, for example.

It will be appreciated that the signals that are produced by the channels, or projection data derived therefrom are generally indicative of information (e.g., indicative of the attenuation of radiation) and small errors (e.g., indicative of signal variations caused by shadowing). Such errors are not relevant for reconstructing an image and may reduce the quality of an image yielded from the signal, for example. To improve the performance of the scanner and/or reduce the effects of signal variations, a calibration procedure is routinely (e.g., daily, weekly, etc.) performed on radiation scanners. During the calibration procedure, a sequence of one or more calibration scans (e.g., a scan in which no object is present in the examination region 116) is performed. Because the radiation 114 that is emitted during the calibration scan is not attenuated by an object (e.g., 112 in FIG. 1), differences in signals produced by a first channel relative to signals produced by a second, neighboring channel, for example, are generally indicative of signal error. In one embodiment, successive scans in the calibration sequence may be collected with the focal spot manually translated through a range expected during an examination. Thus, as will be described in the next few paragraphs, one or more measurements can be taken for the respective channels and baseline characteristics of the errors in signals generated by the respective channels can be determined.

In the example scanner 100, a calibration component 122 is configured to receive projection data yielded from signals generated during a calibration scan and to identify information, or make measurements, for example, from signals that are generated by the respective channels during the calibration scan. In this way, the calibration component 122 can determine a baseline signal for respective channels (e.g., similar to determining an offset on a scale that will cause the scale to read zero before weight is applied). The calibration component 122 is also configured to store the identified information, or measurements, for later use during an examination of the object 112, for example. In one embodiment, the identified information is stored in one or more air tables (also referred to as calibration tables) within a storage medium, for example.

The example scanner 100 also comprises a correction component 124 configured to receive projection data that is yielded from signals generated during an examination of the object 112. As will be discussed in more detail with respect to FIG. 8, the correction component 124 is also configured to use the measurements or other information acquired from signals generated by respective channels during the calibration scan (and stored in the air table(s) by the calibration component 122) and/or from signals generated by calibration channels of the detector array 110 during the examination scan, to reduce the effect of errors in signals generated by imaging channels of the detector array 110 during the examination scan, for example. Stated differently, the correction component 124 is configured to determine the orientation of the focal spot 107 during the examination scan, or rather during a particular view and make corrections to the air table(s) based upon the determined orientation of the focal spot. Using the corrected air table(s), the correction component 124 can substantially isolate (or subtract out) the error from the information portion of the signals generated by respective imaging channels of the detector array 110, for example.

The example scanner 100 further comprises an image reconstructor 126 configured to receive the corrected projection data that is output by the correction component 124. The image reconstructor 126 is configured to generate image data from the projection data using a suitable analytical, iterative, and/or other reconstruction technique (e.g., backprojection reconstruction, tomosynthesis reconstruction, etc.). In this way, the corrected projection data may be converted into a format that may be more suitable for viewing by a human observer.

The image data can be presented on a monitor 128 for human observation. In one embodiment, the monitor 128 displays a user interface, and a computer, connected to the monitor 128, is configured to receive human input. The received input may be transmitted to a controller 130 configured to generate instructions for the object scanning apparatus 102. For example, a doctor may want to view a higher resolution image of the object 112, and the controller 130 can thus instruct the object scanning apparatus 102 to rescan the object 112.

Figure 2:
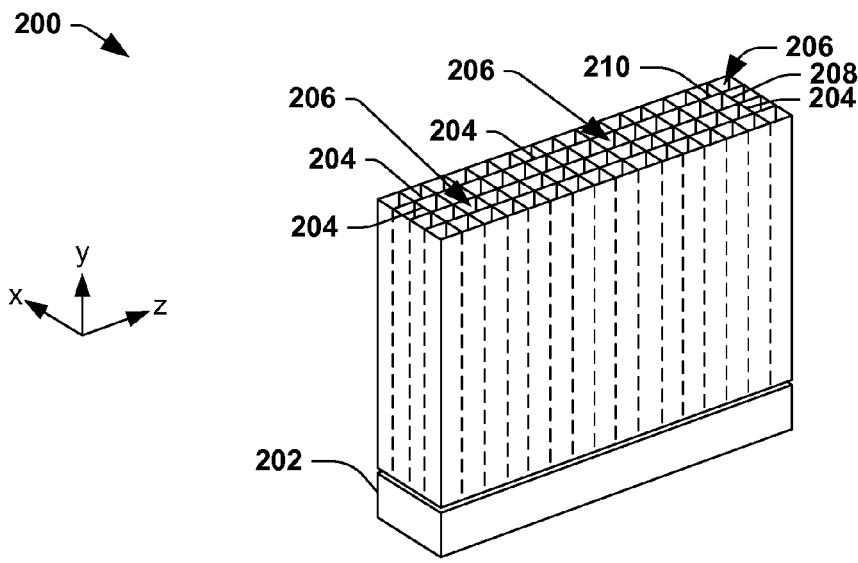
FIG. 2 illustrates an example two-dimensional anti-scatter module.

FIG. 2 illustrates an example anti-scatter module 200 that may be part of an anti-scatter grid (e.g., 118 in FIG. 1). Such an anti-scatter module 200 may be positioned above an underlying detector array 202 (e.g., 110 in FIG. 1) and (optionally) attached to the detector array 202 and/or another portion of an object scanning apparatus (e.g., 102 in FIG. 1), such as a wall of a rotating gantry portion (e.g., 104 in FIG. 1) of the object scanning apparatus, for example.

The anti-scatter module 200 comprises a plurality of anti-scatter plates 204 (e.g., blade-like objects that appear to be protruding from a detector surface of the detector array 202) and transmission channels 206, or openings, between the respective anti-scatter plates 204. The anti-scatter plates 204 are configured to absorb, attenuate, or otherwise alter secondary radiation so that it is not detected by channels of the detector array 202 and can be composed of molybdenum, tungsten, lead, and/or any other material that has characteristics that make it able to absorb, or otherwise alter radiation striking the anti-scatter plates 204. The transmission channels 206 are configured to allow primary radiation to pass through the anti-scatter module 200 and be detected by the underlying detector array 202. In this way, primary radiation can pass through the anti-scatter module 200 while secondary radiation is absorbed, for example, so that it is not detected by the underlying detector array 202.

It will be understood to those skilled in the art that the anti-scatter module 200 depicted in FIG. 2 is a two-dimensional (2-d) anti-scatter module. That is, the anti-scatter module 200 is comprised of both z-axis anti-scatter plates and x-axis anti-scatter plates. It will be appreciated that z-axis anti-scatter plates are used herein to refer to plates that have more surface area laying in an x,y plane than in a y,z plane, and x-axis anti-scatter plates are used herein to refer to anti-scatter plates that have more surface area laying in a y,z plane than in an x,y plane. For example, in the illustrated two-dimensional anti-scatter grid 200, anti-scatter plate 208 would be a z-axis anti-scatter plate and anti-scatter plate 210 would be an x-axis anti-scatter plate. That is, the z-axis anti-scatter plate 208 is substantially in the x, y plane (although it does have a little thickness that extends in the z direction), and the x-axis anti-scatter plate 210 is substantially in the y,z plane (although it does have a little thickness that extends in the x direction). While reference is made to x-axis and z-axis anti-scatter plates, it will be appreciated that x-axis anti-scatter plates can have an x-dimension component and z-axis anti-scatter plates can have a z-dimension component. For example, an anti-scatter plate may be in the shape of an "L" and be referred to as both an x-axis anti-scatter plate and a z-axis anti-scatter plate.

Figure 3:
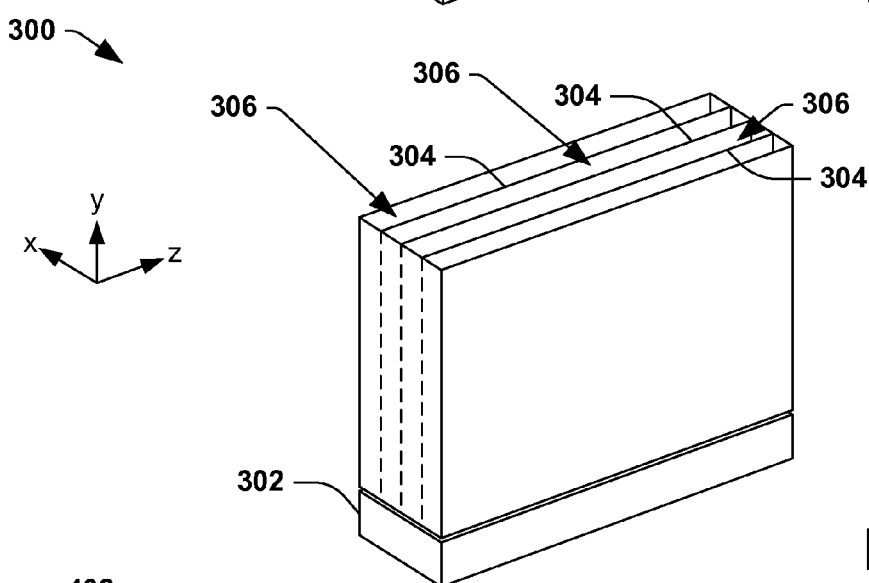
FIG. 3 illustrates an example one-dimensional anti-scatter module.

FIG. 3 illustrates another embodiment of an anti-scatter module 300 that may be part of an anti-scatter grid (e.g., 118 in FIG. 1) positioned above an underlying detector array 302 (e.g., 110 in FIG. 1). As illustrated, the anti-scatter module 300 is a one-dimensional anti-scatter module comprised of a plurality of x-axis anti-scatter plates 304. It will be understood to those skilled in the art that because the there are no z-axis anti-scatter plates, transmission channels 306 comprised in a one-dimensional anti-scatter module, such as the anti-scatter module 300, are generally elongated relative to the transmissions channels 206 comprised within a two-dimensional anti-scatter module, such as the anti-scatter module 200 illustrated in FIG. 2. It will be appreciated that in yet another embodiment, the anti-scatter module 300 can be comprised of z-axis anti-scatter plates 204 but not x-axis anti-scatter plates.

Figure 4:
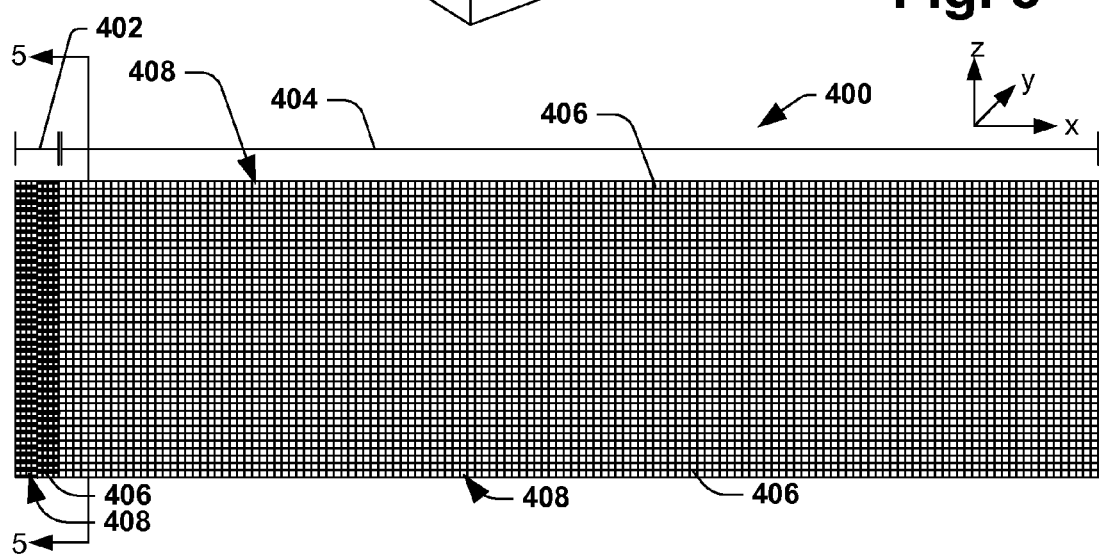
FIG. 4 illustrates a top-down view of an example anti-scatter grid.

FIG. 4 illustrates a top-down view (e.g., looking down from an intended focal spot) of an anti-scatter grid 400 (e.g., 118 in FIG. 1) that may be positioned above an underlying detector array (e.g., 110 in FIG. 1), for example. As illustrated, the anti-scatter grid 400 is a two-dimensional anti-scatter grid comprised of a plurality of anti-scatter modules similar to the anti-scatter module 200 depicted in FIG. 2. It will be appreciated that in another embodiment, the anti-scatter grid can be a one-dimensional anti-scatter module comprised of a plurality of anti-scatter modules similar to the anti-scatter module 300 depicted in FIG. 3, for example. Further, in yet another embodiment, the anti-scatter grid may comprise a single module (e.g., extending across a substantial portion of the detector array).

It will be understood to those skilled in the art that radiation sources are generally designed to emit radiation from a designated location (e.g., the intended focal spot). While radiation is not always emitted from the designated location (e.g., because of thermal drift, g-forces, etc.), generally, the curvature and position of a detector array, the orientation of the anti-scatter plates, etc. are designed based on the designated location. It will be appreciated that this designated location generally does not change (e.g., unless the radiation source is replaced with a new radiation source that has new design specifications, including a new designated focal spot location). Thus the terms "intended focal spot" are used herein to refer to this designated location on the radiation source 108 and not necessarily the actual location of the focal spot (e.g., 107 in FIG. 1) at a given time.

As illustrated, the anti-scatter grid 400 is comprised of a first set 402 of anti-scatter plates 406 (e.g., 204 in FIG. 2) that are focused on one or more points other than an intended focal spot of a radiation source (e.g., 108 in FIG. 1) (hereinafter referred to as defocused anti-scatter plates) and a second set 404 of anti-scatter plates 406 that are focused on the intended focal spot of the radiation source (hereinafter referred to as focused anti-scatter plates). It will be appreciated that the term "set" is used herein in a broad sense to mean one or more anti-scatter plates. It will also be appreciated that when the anti-scatter grid 400 is viewed from the intended focal spot, transmission channels 408 spatially proximate to (e.g., adjacent to) the defocused anti-scatter plates appear to be smaller than transmission channels 408 that are spatially proximate to the focused anti-scatter plates because a greater portion (e.g., sidewalls) of the defocused anti-scatter plates can be visible. Stated differently, as will be described in detail with respect to FIGS. 5-6, the first set 402 of anti-scatter plates 406 (the defocused anti-scatter plates) may be angled with respect to the intended focal spot, and thus both the top and a side portion of the respective anti-scatter plates 406 may be visible when viewing the anti-scatter grid 400 from the intended focal spot. The transmission channels 408 that are spatially proximate to the second set 404 anti-scatter plates 406 may appear larger because the top of the respective anti-scatter plates 406 (but not the side) may be visible when viewing the anti-scatter grid 400 from the intended focal spot, for example.

It will be appreciated that because the first set 402 of anti-scatter plates 406 (the defocused anti-scatter plates) are not focused on the intended focal spot, shadows may be imposed on channels that are in close spatial proximity to respective defocused anti-scatter plates when the focal spot (e.g., 107 in FIG. 1) is actually located at the intended focal spot. It will also be appreciated that the terms "calibration channel" are used herein to refer to a channel in close spatial proximity to a defocused anti-scatter plate (e.g., a calibration channel is a channel that is shadowed by a defocused anti-scatter plate), and the terms "imaging channel" are used herein to refer to a channel in close spatial proximity to a focused anti-scatter plate. As will be discussed below, such shadowing is beneficial because signals generated by a calibration channel can be used to identify the orientation of the focal spot (e.g., 107 in FIG. 1), or a change in the orientation of the focal spot.

Figure 5:
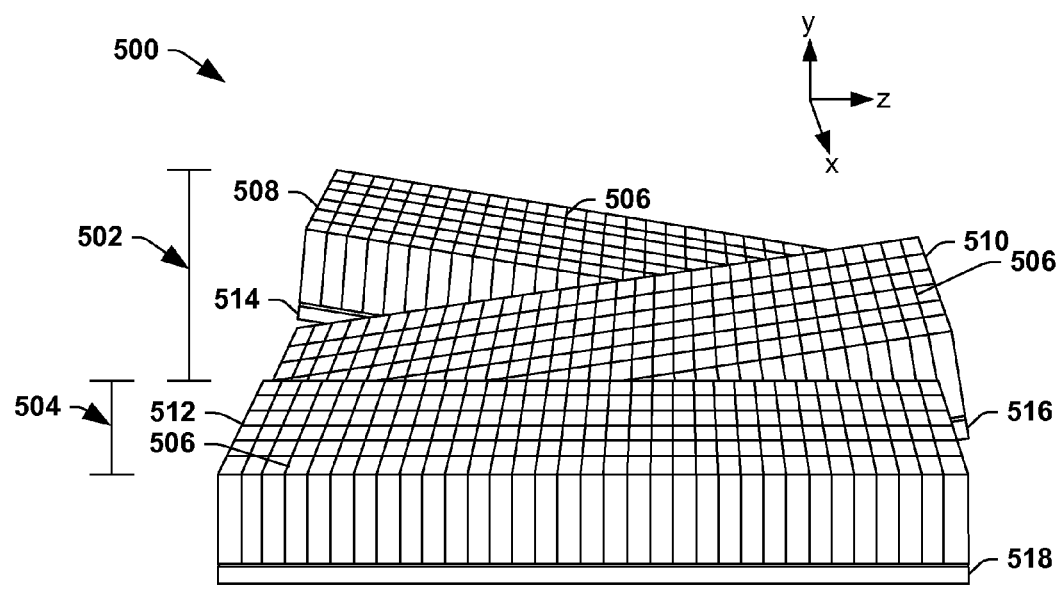
FIG. 5 illustrates a cross-sectional view of an example anti-scatter grid.

FIG. 5 illustrates a cross-section (along 5-5 in FIG. 4) of an anti-scatter grid 500 (e.g., 400 in FIG. 4) wherein a first set 502 (e.g., 402 in FIG. 4) of anti-scatter plates 506 (e.g., 406 in FIG. 4) are focused on one or more points other than an intended focal spot of a radiation source (e.g., 108 in FIG. 1) and a second set 504 (e.g., 404 in FIG. 4) of the anti-scatter plates 506 are focused on the intended focal spot. More particularly, FIG. 5 illustrates three anti-scatter modules 508, 510, 512 (e.g., similar to the anti-scatter module 200 depicted in FIG. 2) of the anti-scatter grid 500 that are positioned above respective detector modules 514, 516, 518, the detector modules 514, 516, 518 configured to detect radiation that traverses the respective anti-scatter modules 508, 510, 512. Stated differently, a first anti-scatter module 508 is positioned above a first detector module 514 that is configured to detect radiation that has traversed the first anti-scatter module 508, a second anti-scatter module 510 is positioned above a second detector module 516 that is configured to detect radiation that has traversed the second anti-scatter module 510, etc.

As illustrated, the third anti-scatter module 512 (e.g., the module closest to the cross-section 5-5) and third detector module 518 are focused on the intended focal spot (not shown) which is substantially centered on the page and positioned above the third anti-scatter module 512. The first and second anti-scatter modules 508, 510 and respective first and second detector modules 514, 516 are tilted with respect to the third anti-scatter module 512 and third detector module 518. In this way, anti-scatter plates 506 comprised within the first and second anti-scatter modules 508 and 510 (e.g., the first set 502 of anti-scatter plates 506) are not focused on the intended focal spot.

It will be appreciated that as illustrated, the first and second anti-scatter modules 508, 510 and respective first and second detector modules 514, 516 are tilted in the z-dimension relative to the third anti-scatter module 512 because focal spot motion generally occurs in the z-dimension, for example. In other embodiments (e.g., where focal spot motion occurs in the x-dimension) the first and/or second anti-scatter modules 508, 510 and respective first and/or second detector modules 514, 516 can be tilted in the x-dimension. For example, in another embodiment, the first anti-scatter module 508 and the first detector module 514 can be titled in the x-dimension, and the second anti-scatter module 510 and the second detector module 516 can be titled in the z-dimension. In this way, change in the orientation of the focal spot in both the x- and z-dimensions can be more easily detected (relative to if both anti-scatter modules 508, 510 were tilted in the same dimension).

It will also be appreciated that the first and second anti-scatter modules 508 and 510, and the first and second detector modules 514, 516 respectively, are tilted in opposite directions relative to the intended focal spot. Stated differently, the first anti-scatter module 508 and the first detector module 514 are titled in a first direction and the second anti-scatter module 510 and the second detector module 516 are titled in a second direction. In one embodiment, the first and second anti-scatter modules 508, 510, and the first and second detector modules 514, 516 respectively, are tilted the same number of degrees away from center (e.g., where center is the intended focal spot). In this way, the first detector module 514 detects the inverse of what the second detector module 516 detects (and the gains in signals generated by calibration channels comprised in the first detector module 514 offset losses in signals generated by calibration channels comprised in the second detector module 516). For example, a change in the orientation of the focal spot may cause shadows detected by the first detector module 514, tilted in the first direction, to increase by five millimeters and may cause shadows detected by the second detector module 516, tilted in the second direction, to decrease by five millimeters.

Further, it will be appreciated that more than or less than two anti-scatter modules can be tilted with respect to remaining anti-scatter modules that comprise anti-scatter plates that focused on the intended focal spot (e.g., the second set 404 of anti-scatter plates 406 in FIG. 4). For example, in another embodiment, a single anti-scatter module is tilted with respect to the remaining modules.

Figure 6:
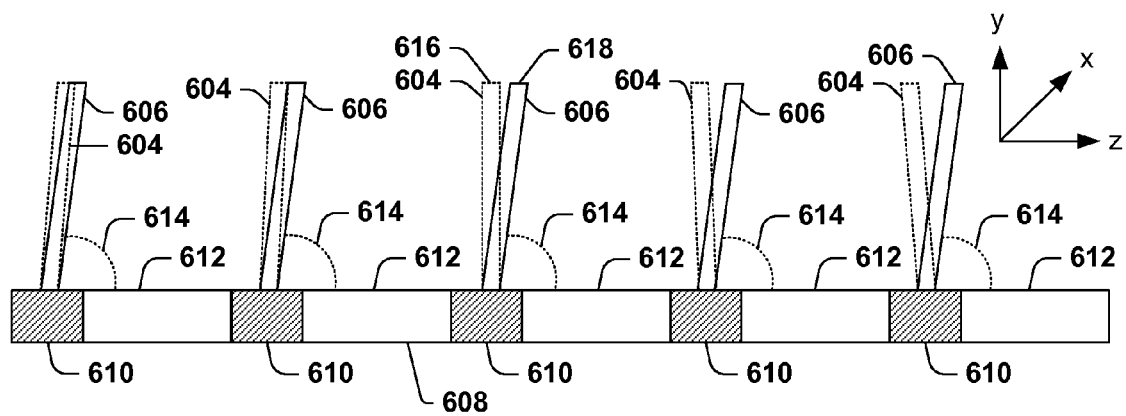
FIG. 6 illustrates a plurality of defocused anti-scatter plates.
Figure 7:
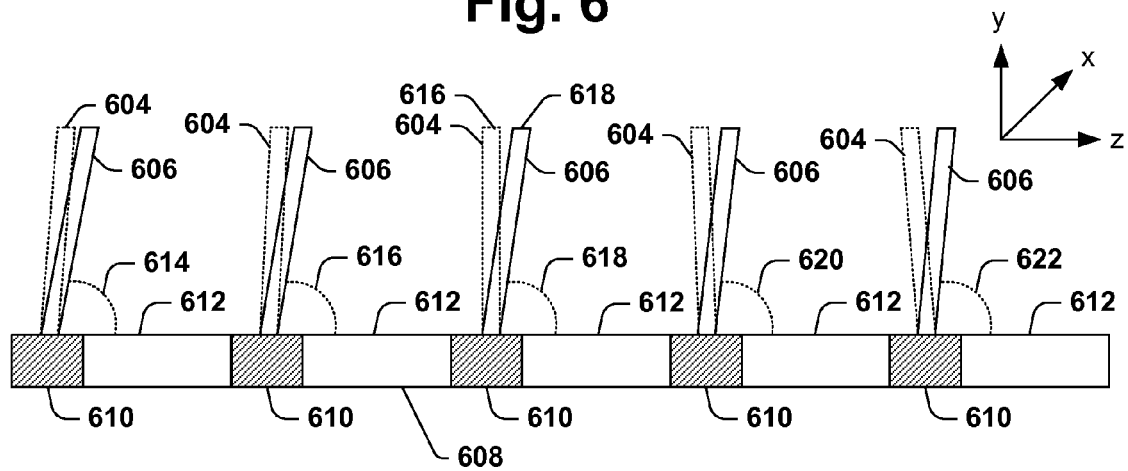
FIG. 7 illustrates a plurality of defocused anti-scatter plates.

FIGS. 6-7 illustrate defocused anti-scatter plates 606. Such anti-scatter plates may be part of an anti-scatter grid (e.g., 400 in FIG. 1). In one embodiment, where the anti-scatter grid is comprised of defocused anti-scatter plates 606 as described with respect to FIGS. 6 and/or 7, one or more anti-scatter modules may not be tilted as described in FIG. 5. Stated differently, instead of tilting anti-scatter modules, for example, a portion of the anti-scatter grid may be manufactured, for example, such that the anti-scatter plates 606 are themselves oriented differently than they would be in a conventional anti-scatter grid. The defocused anti-scatter plates 606 are generally positioned above gaps 610 (e.g., areas that do not detect radiation) of an underlying detector array 608 (e.g., 110 in FIG. 1). Adjacent respective gaps 610 are channels 612 of the detector array 608 that are configured to detect radiation.

It will be appreciated that to distinguish the orientation of conventional anti-scatter plates from the orientation of the defocused anti-scatter plates, FIGS. 6-7 illustrate both conventional anti-scatter plates 604 (e.g., focused on the intended focal spot), represented by dotted lines, and defocused anti-scatter plates 606, represented by solid lines. The conventional anti-scatter plates 604 are focused on an intended focal spot of the radiation source (not shown). Thus, generally a center anti-scatter plate 616, or rather a center row (running parallel to the x-axis) of anti-scatters plates are perpendicular in the z-dimension to a detection surface of the detector array 608. It will be appreciated that the term "center" is used broadly herein to describe a plate or row that that substantially passes through an x,y plane extending through the intended focal spot. While the center row generally describes a middle row (running parallel to the x-axis) of the anti-scatter grid, it may not be in the middle of the anti-scatter grid depending upon the orientation of the intended focal spot relative to the orientation of the anti-scatter grid. Conventional anti-scatter plates 604 that are positioned on either side of the center anti-scatter plate 616, are generally titled inward (e.g., toward the center plate 616). In this way, respective anti-scatter plates 604 are focused on the intended focal spot that is positioned above the center anti-scatter plate 616. It will be appreciated that because the anti-scatter plates 604 are convergent on a single point, the intended focal spot, anti-scatter plates 604 that are in a row running parallel to the z-axis are not in parallel.

As illustrated in FIG. 6, in one embodiment wherein the defocused anti-scatter plates 606 are oriented differently than similarly positioned conventional anti-scatter plates 604, respective defocused anti-scatter plates 606 may be angled at a substantially similar angle, gamma 614, with respect to a detection surface of the detector array 608. It will be appreciated that gamma 614 may be a function of focal spot motion tolerance. For example, if it is estimated that the focal spot can move in a 5 mm radius about the intended focal spot, gamma 614 may be defined such that a defocused anti-scatter plate in the center row 618 is angled at a point 7 mm away from the focal spot in the z-dimension.

It will be appreciated that, as illustrated in FIG. 6, the defocused anti-scatter plate in the center row 618 is angled an at angle other than ninety degrees in the z-dimension relative to the detection surface of the detector array because the defocused anti-scatter plate 618 is not focused on the intended focal spot. Further, because the anti-scatter plates 606 are angled at a substantially similar angle, the anti-scatter plates are non-convergent. That is, they are not focused on a single point, but rather may be focused on infinity, for example.

FIG. 7 illustrates another embodiment wherein defocused anti-scatter plates 606 are oriented differently than similarly positioned traditional anti-scatter plates 604. More particularly, whereas FIG. 6 illustrates non-convergent, defocused anti-scatter plates 606, FIG. 7 illustrates convergent, defocused anti-scatter plates 606. Thus, the anti-scatter plates 606 are (all) focused on a single point that is not the intended focal spot. Stated differently, respective plates 606 are angled at different angles 614, 616, 618, 620, and 622 such that the respective plates 606 are focused on the same point. Further, similar to FIG. 6, the defocused anti-scatter plate in the center row 618 is angled an at angle other than ninety degrees in the z-dimension relative to the detection surface of the detector array 608 because the defocused anti-scatter plate 618 is not focused on the intended focal spot.

It will be appreciated that the orientation of the point may be a function of potential focal spot motion. For example, if focal spot tolerance permits the focal spot to move in a 5 mm radius away from the intended focal spot, the point that the defocused anti-scatter plates 606 are focused on may be a point 6-7 mm away from the intended focal spot. In this way, the possibility that defocused anti-scatter plates 606 will ever be focused on the actual focal spot (e.g., 107 in FIG. 1) is reduced, for example. Further, while the defocused anti-scatter plates 606 illustrated in FIG. 7 are angled at an acute angle relative to the detection surface of the detector array 608, in another example, a portion (or all) of the anti-scatter plates 606 may be angled at an obtuse angle depending upon the orientation of the point (relative to respective defocused anti-scatter plates 606).

It will be understood to those skilled in the art that while FIGS. 6-7 merely illustrate five defocused anti-scatter plates 606 positioned along a single row (parallel to a z-axis) of the anti-scatter grid, as illustrated in FIG. 4, the anti-scatter grid may comprise a plurality of rows. Respective rows can comprise more or less anti-scatter plates than the five anti-scatter plates illustrated herein. Further, the anti-scatter grid may comprise both conventionally oriented anti-scatter plates 604 (as illustrated by the dashed-line anti-scatter plates in FIGS. 6-7) and defocused anti-scatters plates 606 (e.g., as illustrated by the solid-lined anti-scatter plates in FIGS. 6-7).

Figure 8:
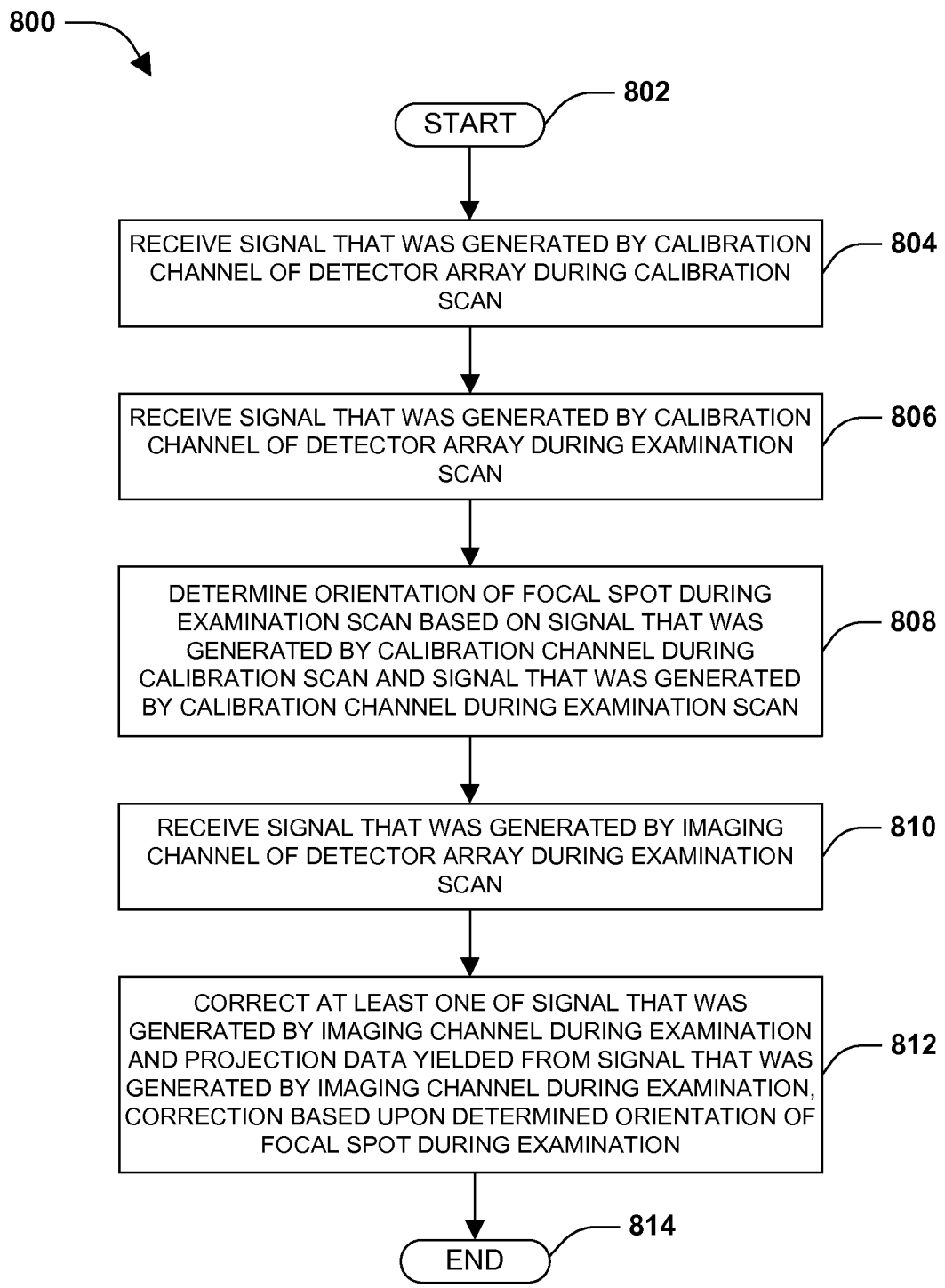
FIG. 8 is a flow diagram illustrating an example method for determining the orientation of a focal spot and for correcting one or more signals generated by an imaging channel(s) of a detector array.

FIG. 8 illustrates an example method 800. Such a method 800 can be used to reduce the effects of shadowing or focal spot motion on a radiographic image, for example. The example method 800 begins at 802 and signals are received (e.g., by a calibration component 122 in FIG. 1) from one or more calibration channels of a detector array during a calibration scan, or a sequence of calibration scans, at 804. It will be appreciated that the terms "calibration channels" are used herein to broadly refer to channels that are in close spatial proximity to (e.g., adjacent to) one or more anti-scatter plates that are focused on a point other than an intended focal spot. As will be discussed below, signals generated from such channels are useful for determining the orientation, or position, of the focal spot and may or may not also be useful for generating an image of the object.

Anti-scatter plates may be aligned with a point other than the intended focal spot in numerous ways. For example, in one embodiment, as illustrated in FIG. 5, one or more anti-scatter modules may be tilted with respect to remaining anti-scatter modules of an anti-scatter grid such that anti-scatter plates comprised within the anti-scatter module are aligned with a point other than an intended focal spot. The anti-scatter plates comprised in the remaining anti-scatter modules can be focused on the intended focal spot. In another embodiment, as illustrated in FIGS. 6-7, the defocused anti-scatter plates can be oriented differently than they would be oriented if they were focused on the intended focal spot.

It will be appreciated that the anti-scatter plates that are aligned with a point other than the intended focal spot are configured to cast shadows on respective calibration channels during the calibration scan and/or examination scan(s). These shadows are detected by the calibration channels, and signals emitted from the respective calibration channels are indicative of the size of the shadows detected by the respective calibration channels. Thus, the signals received from the one or more calibration channels during the calibration scan are indicative of the size of shadows detected by respective calibration channels during the calibration scan.

As discussed with respect to FIG. 1, signals generated by the calibration channels during the calibration scans, or projection data generated therefrom, can be measured to determine the change (e.g., error) in the respective signals and/or to establish a baseline signal, for example. It will be appreciated that the change in the respective signals is related to the size of the shadow, so such measurements can also be used to determine the size of shadow imposed on respective calibration channels during the calibration scan, for example. Such measurements can be stored in an air table(s) in a storage medium, for example. As will be discussed below, in this way, changes in orientation, or size, of the shadows detected during the calibration and the shadows detected during a later examination can be compared to determine whether and/or how the focal spot has moved, for example.

At 806, signals from the one or more calibration channels of the detector array are received (e.g., by the correction component 124 in FIG. 1) during an examination scan. These signals are indicative of shadows cast during the examination by respective anti-scatter plates that are aligned with a point other than the intended focal spot and are generated by respective calibration channels in response to the detection of the shadows by the respective calibration channels.

At 808, the position, or orientation, of a focal spot during the examination is determined (e.g., by the correction component 124 in FIG. 1) based on signals from the one or more calibration channels that were received during the calibration scan(s) and the signals from the one or more calibration channels that were received during the examination scan. For example, in one embodiment, the measurements of signals generated by respective calibration channels during the examination scan are compared with the measurements of signals generated by the respective calibration channels during a sequence of calibration scans that were stored in the air table(s). By comparing the measurements, or the average of the measurements, taken during the calibration scan with the measurements, or average of the measurements, taken during the examination, it can be determined how the orientation of the focal spot changed.

Stated differently, the size and orientation of shadows cast from the defocused anti-scatter plates are a function of the orientation of the focal spot. When the orientation of the focal spot changes, the size and/or orientation of shadows cast from the anti-scatter plates that are focused on a point other than the intended focal spot change in a predictable manner. Thus, by determining how the shadows change (based upon changes in the signals, or rather measurements taken of the signals) between the calibration scan and the examination scan, it can be determined how the orientation of the focal spot changed.

At 810, signals from one or more imaging channels of the detector array are received during the examination scan. It will appreciated that the terms "imaging channels" are used broadly herein to refer to channels that are in close spatial proximity to one or more anti-scatter plates that are aligned with the intended focal spot and/or are configured to generate signals from which an image of an object under examination may be determined. Such channels are generally are less shadowed than calibration channels when the focal spot is at the intended focal spot.

At 812, the signals received during the examination scan from the one or more imaging channels and/or projection data yielded from such signals, are corrected (e.g., by the correction component 124 in FIG. 1) based upon the determined position of the focal spot during the examination scan. In this way, measurements that are taken during the calibration process to established a baseline signal (e.g., as discussed with respect to the background and FIG. 1) can be updated to take into consideration the change in the orientation of the focal spot between the calibration scan and the examination scan.

Stated differently, during the sequence of calibration scans, or scan, imaging channels can also generate signals, which can be measured to determine the amount of error in signals emitted for the respective channel and/or establish a baseline signal for respective channels. Such measurements are dependent upon the orientation of the focal spot. Thus, if the orientation of the focal spot changes, the measurements taken during the orientation are less relevant for isolating the noise from an information carrying portion of the signal because the noise has changed (e.g., the baseline that was determined from the calibration scan is no longer the baseline). Therefore, to make the measurements relevant in light of the changed orientation of the focal spot, the measurements taken during the calibration scan that are indicative of signals generated by the imaging channels are adjusted to reflect measurements that would have been acquired had the focal spot been orientated in a way that was substantially similar to the orientation of the focal spot at the time of the examination.

It will be appreciated that because the orientation of the focal spot is determined based upon signals generated by the calibration channels, the orientation of the focal spot can be determined on a view-by-view basis (even on high-quality imaging scanners and/or scanners that rotate rapidly) because fewer mathematical algorithms are required to be performed, for example (e.g., relative to the mathematical algorithms required to determine the orientation of the focal spot from a pinhole camera image). Further, the correction systems and/or techniques herein disclosed may be more precise than correction systems and/or techniques known to those skilled in the art, such as the pinhole camera correction technique, for example, because actual changes in shadows imposed upon calibration channels are able to be identified, or measured. Thus, the orientation of the focal spot is not determined based upon an estimated location of a center beam of radiation from a picture depicting the radiation, but rather it is based upon actual changes in the shadows.

The example method 800 ends at 814.

Figure 9:
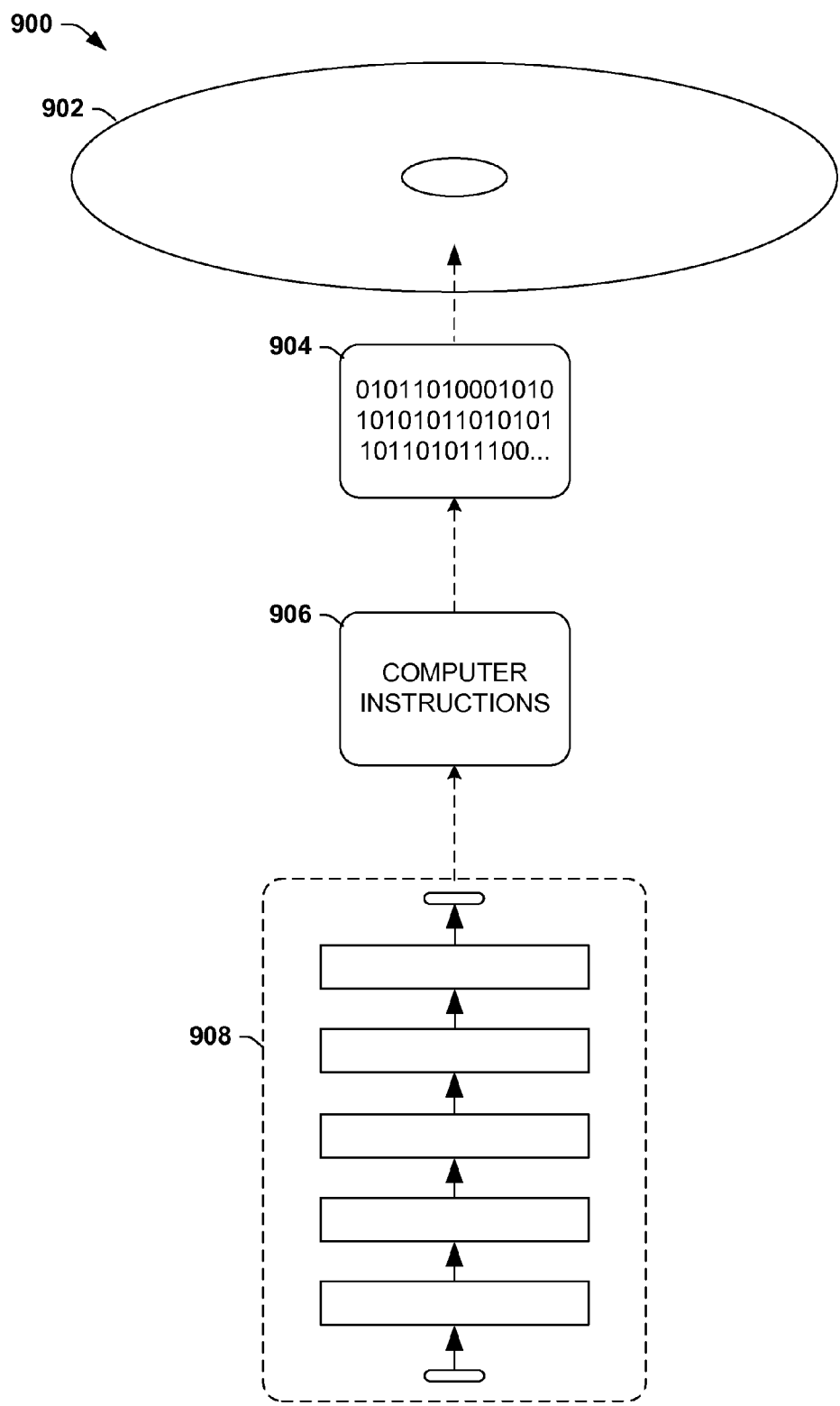
FIG. 9 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 9, wherein the implementation 900 comprises a computer-readable medium 902 (e.g., a CD-R, DVD-R, or a platter of a hard disk drive), on which is encoded computer-readable data 904. This computer-readable data 904 in turn comprises a set of computer instructions 906 configured to operate according to one or more of the principles set forth herein. In one such embodiment 900, the processor-executable instructions 906 may be configured to perform a method 908, such as the example method 800 of FIG. 8, for example. In another such embodiment, the processor-executable instructions 906 may be configured to implement a system, such as at least some of the exemplary scanner 100 of FIG. 1, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A radiography scanning apparatus, comprising:
a radiation source configured to emit radiation;
a detector array configured to detect the emitted radiation; and
an anti-scatter grid comprised of a plurality of anti-scatter plates, wherein a first set of anti-scatter plates are focused on a point other than an intended focal spot of the radiation source, and wherein a second set of anti-scatter plates are focused on the intended focal spot, the second set different than the first set.

2. The apparatus of claim 1, wherein the anti-scatter grid is a two-dimensional (2-d) anti-scatter grid and the first set of anti-scatter plates are z-axis anti-scatter plates.

3. The apparatus of claim 2, wherein the 2-d anti-scatter grid comprises a plurality of anti-scatter modules, wherein at least one anti-scatter module is tilted in the z-dimension relative to remaining anti-scatter modules of the 2-d anti-scatter grid.

4. The apparatus of claim 3, wherein at least a first and second anti-scatter module are tilted in the z-dimension relative to remaining anti-scatter modules of the 2-d anti-scatter grid, the first anti-scatter module titled in a first direction and the second anti-scatter module tilted in a second direction, the second direction different than the first direction.

5. The apparatus of claim 2, wherein a first anti-scatter plate of the first set of anti-scatter plates is positioned in a center row parallel to an x-axis and is angled at an angle other than ninety degrees in the z-dimension relative to an underlying detector surface of the detector array.

6. The apparatus of claim 5, wherein anti-scatter plates that comprise the first set of anti-scatter plates are substantially parallel.

7. The apparatus of claim 1, wherein the detector array is comprised of at least one calibration channel, the calibration channel in close spatial proximity to a first anti-scatter plate of the first set of anti-scatter plates and configured to generate signals indicative of an orientation of a focal spot.

8. The apparatus of claim 7, comprising a correction component configured to identify a change in the orientation of the focal spot between a calibration scan and an examination based upon the signals generated by the calibration channel.

9. The apparatus of claim 1, wherein the detector array comprises at least one calibration channel and at least one imaging channel, wherein the calibration channel is in close spatial proximity to an anti-scatter plate of the first set of anti-scatter plates and the imaging channel is in close spatial proximity to an anti-scatter plate of the second set of anti-scatter plates.

10. The apparatus of claim 9, comprising:
a correction component configured to correct at least one of a signal generated by the imaging channel during an examination and projection data yielded from the signal generated by the imaging channel during the examination scan based upon a signal generated by the calibration channel during the examination.

11. The apparatus of claim 1, wherein a third set of anti-scatter plates are focused on a second point other than the intended focal spot, the third set different than the first set and the second set.

12. A method, comprising:
receiving a signal that was generated by a calibration channel of a detector array during a calibration scan;
receiving a signal that was generated by the calibration channel of the detector array during an examination scan;
determining an orientation of a focal spot during the examination based on the signal that was generated by the calibration channel during the calibration scan and the signal that was generated by the calibration channel during the examination;
receiving a signal that was generated by an imaging channel of the detector array during the examination; and
correcting at least one of the signal that was generated by the imaging channel during the examination and projection data yielded from the signal that was generated by the imaging channel during the examination, the correction based upon the determined orientation of the focal spot during the examination.

13. The method of claim 12, comprising:
detecting a first shadow cast on the calibration channel during the calibration scan, the first shadow cast from an anti-scatter plate that is focused on a point other than an intended focal spot;
generating a first signal at the calibration channel in response to the detected first shadow;
detecting a second shadow cast on the calibration channel during the examination, the second shadow cast from the anti-scatter plate that is focused on a point other than the intended focal spot; and
generating a second signal at the calibration channel in response to the detected second shadow.

14. The method of 12, wherein determining comprises comparing the signal generated by the calibration channel during the calibration scan with the signal generated by the calibration channel during the examination.

15. The method of claim 12, comprising aligning a first set of anti-scatter plates on a first point other than an intended focal spot of a radiation source.

16. The method of claim 15, comprising aligning a second set of anti-scatter plates on a second point other than the intended focal spot of the radiation source, wherein the second point and first point are substantially spaced an equal distance away from the intended focal spot, wherein the first point, the second point, and the intended focal spot lay on a z-axis, the intended focal spot laying between the first point and the second point.

17. The method of claim 12, comprising identifying one or more changes in the signal received from the calibration channel during the examination relative to the signal received from the calibration channel during the calibration.

18. The method of claim 17, wherein the orientation of the focal spot is determined based upon the identified one or more changes.

19. A radiography scanning apparatus, comprising:
a radiation source configured to emit radiation;
an anti-scatter grid comprised of at least first and second sets of anti-scatter plates, the first set comprising anti-scatter plates that are focused on a point other than an intended focal spot of the radiation source and the second set comprising anti-scatter plates that are focused on the intended focal spot of the radiation source;
a detector array configured to detect the emitted radiation, the detector array comprising calibration channels and imaging channels, respective calibration channels positioned in close spatial proximity to an anti-scatter plate that is focused on the point other than the intended focal spot of the radiation source and respective imaging channels positioned in close spatial proximity to an anti-scatter plate that is focused on the intended focal spot of the radiation source, the calibration channels respectively configured to generate signals indicative of an orientation of a focal spot; and
a correction component configured to identify a change in the orientation of the focal spot between a calibration scan and an examination based upon the signals generated by the calibration channels.

20. The apparatus of claim 19, wherein the anti-scatter grid is a two-dimensional (2-d) anti-scatter grid and the first set of anti-scatter plates are z-axis anti-scatter plates.

* * * * *